(12) United States Patent
Blankenship

(10) Patent No.: US 7,011,646 B2
(45) Date of Patent: Mar. 14, 2006

(54) BALLOON CATHETER HAVING A BALLOON WITH A THICKENED WALL PORTION

(75) Inventor: Delma M. Blankenship, Sunnyvale, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 305 days.

(21) Appl. No.: 10/602,584

(22) Filed: Jun. 24, 2003

(65) Prior Publication Data

US 2004/0267197 A1 Dec. 30, 2004

(51) Int. Cl.
*A61M 31/00* (2006.01)
*A61M 37/00* (2006.01)

(52) U.S. Cl. .............................. 604/103.06; 604/96.01; 606/194

(58) Field of Classification Search ........... 604/103.06, 604/103.07, 103.11, 103.01, 103.04, 103.05, 604/103, 96.01, 915, 916, 917, 918, 919, 604/920, 95.03, 98.01, 508; 606/192, 194
See application file for complete search history.

(56) References Cited

U.S. PATENT DOCUMENTS

| | | | | |
|---|---|---|---|---|
| 5,087,394 A | * | 2/1992 | Keith ........................... | 264/470 |
| 5,270,086 A | * | 12/1993 | Hamlin ....................... | 428/35.2 |
| 5,344,401 A | * | 9/1994 | Radisch et al. ......... | 604/103.06 |
| 5,409,495 A | * | 4/1995 | Osborn ..................... | 623/1.11 |
| 5,470,313 A | * | 11/1995 | Crocker et al. ......... | 604/103.07 |
| 5,587,125 A | | 12/1996 | Roychowdhury | |
| 5,645,560 A | * | 7/1997 | Crocker et al. ............. | 606/192 |
| 5,711,754 A | | 1/1998 | Miyata et al. | |
| 5,797,877 A | | 8/1998 | Hamilton et al. | |
| 5,807,520 A | | 9/1998 | Wang et al. | |
| 5,810,871 A | * | 9/1998 | Tuckey et al. .............. | 606/198 |
| 5,843,116 A | | 12/1998 | Crocker et al. | |
| 5,868,704 A | | 2/1999 | Campbell et al. | |
| 5,980,532 A | | 11/1999 | Wang | |
| 6,004,289 A | | 12/1999 | Saab | |
| 6,024,722 A | * | 2/2000 | Rau et al. ................. | 604/96.01 |
| 6,024,752 A | * | 2/2000 | Horn et al. ................. | 606/192 |
| 6,120,477 A | | 9/2000 | Campbell et al. | |

(Continued)

FOREIGN PATENT DOCUMENTS

EP 0768097 A2 * 4/1997

(Continued)

*Primary Examiner*—Nicholas Luchessi
*Assistant Examiner*—Theodore John Stigell
(74) *Attorney, Agent, or Firm*—Fulwider Patton LLP

(57) ABSTRACT

A balloon catheter having a balloon with a thickened wall portion extending along at least a portion of the working length section of the balloon in a noninflated configuration. The balloon has a first layer formed of a first polymeric material and a second layer formed of a second, different polymeric material, the second layer having a wall thickness which is greater along the central working length section than the wall thickness of the second layer along a section proximal and/or a section distal to the central working length of the balloon. In a presently preferred embodiment, the first layer is formed of a porous material such as expanded polytetrafluoroethylene (ePTFE), and the second layer of the balloon is formed of an elastomeric polymer. The balloon catheter has a highly flexible distal section and a relatively high strength, low profile balloon, due to the balloon configuration of the invention.

14 Claims, 2 Drawing Sheets

U.S. PATENT DOCUMENTS

| | | | |
|---|---|---|---|
| 6,124,007 A * | 9/2000 | Wang et al. | 428/35.2 |
| 6,242,063 B1 * | 6/2001 | Ferrera et al. | 428/35.2 |
| 6,428,506 B1 | 8/2002 | Simhambhatla et al. | |
| 6,506,202 B1 * | 1/2003 | Dutta et al. | 606/194 |
| 6,641,694 B1 | 11/2003 | Lee | |
| 6,663,614 B1 * | 12/2003 | Carter | 604/525 |
| 6,719,774 B1 | 4/2004 | Wang | |
| 6,863,861 B1 * | 3/2005 | Zhang et al. | 264/530 |
| 2002/0081406 A1 | 6/2002 | Wang et al. | |
| 2004/0044309 A1 * | 3/2004 | Owens et al. | 604/103.06 |
| 2004/0176791 A1 * | 9/2004 | Lim et al. | 606/194 |

FOREIGN PATENT DOCUMENTS

| | | |
|---|---|---|
| WO | WO 01/45766 A1 * | 12/2000 |
| WO | WO 02/081018 A1 * | 4/2002 |

* cited by examiner

BALLOON CATHETER HAVING A BALLOON WITH A THICKENED WALL PORTION

BACKGROUND OF THE INVENTION

This invention generally relates to medical devices, and particularly to intracorporeal devices for therapeutic or diagnostic uses, such as balloon catheters.

In percutaneous transluminal coronary angioplasty (PTCA) procedures, a guiding catheter is advanced until the distal tip of the guiding catheter is seated in the ostium of a desired coronary artery. A guidewire, positioned within an inner lumen of a dilatation catheter, is first advanced out of the distal end of the guiding catheter into the patient's coronary artery until the distal end of the guidewire crosses a lesion to be dilated. Then the dilatation catheter having an inflatable balloon on the distal portion thereof is advanced into the patient's coronary anatomy, over the previously introduced guidewire, until the balloon of the dilatation catheter is properly positioned across the lesion. Once properly positioned, the dilatation balloon is inflated with fluid one or more times to a predetermined size at relatively high pressures (e.g., greater than 8 atmospheres) so that the stenosis is compressed against the arterial wall and the wall expanded to open up the passageway. Generally, the inflated diameter of the balloon is approximately the same diameter as the native diameter of the body lumen being dilated so as to complete the dilatation but not overexpand the artery wall. Substantial, uncontrolled expansion of the balloon against the vessel wall can cause trauma to the vessel wall. After the balloon is finally deflated, blood flow resumes through the dilated artery and the dilatation catheter can be removed therefrom.

In such angioplasty procedures, there may be restenosis of the artery, i.e., reformation of the arterial blockage, which necessitates either another angioplasty procedure, or some other method of repairing or strengthening the dilated area. To reduce the restenosis rate and to strengthen the dilated area, physicians frequently implant a stent inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by inflation of the balloon. The balloon is deflated to remove the catheter, and the stent left in place within the artery at the site of the dilated lesion. Stent covers on an inner or an outer surface of the stent have been used in, for example, the treatment of pseudo-aneurysms and perforated arteries, and to prevent prolapse of plaque. Similarly, vascular grafts comprising cylindrical tubes made from tissue or synthetic materials such as polyester, expanded polytetrafluoroethylene, and DACRON may be implanted in vessels to strengthen or repair the vessel, or used in an anastomosis procedure to connect vessels segments together.

In the design of catheter balloons, characteristics such as strength, compliance, and profile of the balloon are carefully tailored depending on the desired use of the balloon catheter, and the balloon material and manufacturing procedure are chosen to provide the desired balloon characteristics. A variety of polymeric materials are conventionally used in catheter balloons. Use of polymeric materials such as PET that do not stretch appreciably consequently necessitates that the balloon is formed by blow molding, and the deflated blow molded balloon forms wings which are folded around the catheter shaft prior to inflation of the balloon in the patient's body lumen. However, it can be desirable to employ balloons, referred to as formed-in-place balloons, that are not folded prior to inflation, but which are instead expanded to the working diameter within the patient's body lumen from a generally cylindrical or tubular shape (i.e., essentially no wings) that conforms to the catheter shaft. One such balloon which has been suggested is a catheter balloon formed in part of expanded polytetrafluoroethylene (ePTFE). ePTFE is PTFE which has been expanded to form porous ePTFE, and typically has a node and fibril microstructure comprising nodes interconnected by fibrils. However, one difficulty has been forming a flexible, low profile balloon catheter with relatively high strength ePTFE balloon.

It would be a significant advance to provide a catheter balloon, or other expandable tubular medical device, with an improved combination of characteristics such as strength, flexibility, and low profile for improved catheter performance.

SUMMARY OF THE INVENTION

The invention is directed to a balloon catheter having a balloon with a thickened wall portion extending along at least a portion of the working length section of the balloon in a noninflated configuration. The balloon has a first layer formed of a first polymeric material and a second layer formed of a second, different polymeric material. The wall thickness of the second layer along the central working length section is greater than along a section proximal and/or a section distal to the central working length section. In a presently preferred embodiment, the first layer is formed of a porous material such as expanded polytetrafluoroethylene (ePTFE), and the second layer of the balloon is formed of an elastomeric polymer. The balloon catheter of the invention has a highly flexible distal section and a relatively high strength, low profile balloon, due to the balloon configuration of the invention.

In a presently preferred embodiment, the balloon catheter is a stent delivery catheter, with a stent mounted on the balloon for delivering and implanting the stent in a patient's body lumen, although the catheter balloon of the invention is suitable for use in a variety of balloon catheters, which in alternative embodiments of the invention include coronary and peripheral dilatation catheters, drug delivery catheters, and the like. A balloon catheter of the invention generally comprises an elongated shaft having a proximal end, a distal end, and at least one lumen, and a balloon on a distal shaft section with an interior in fluid communication with the at least one lumen of the shaft. The balloon has a proximal skirt section bonded to the shaft, a distal skirt section bonded to the shaft, and an inflatable section therebetween. The balloon has a noninflated configuration (i.e., prior to inflation of the balloon to the working diameter) which inflates to an inflated configuration within the working pressure range. After being inflated, the balloon in the inflated configuration can be deflated to a deflated configuration. The inflatable section of the balloon comprises a central working length section configured to perform a procedure such as dilating a stenosis or expanding a stent, a proximal tapered section between the proximal skirt section and the working length section, and a distal tapered section between the distal skirt section and the working length section. In a presently preferred embodiment, the wall thickness of the balloon second layer along the working length section is greater than the wall thickness of the second layer along at least one of the proximal and distal tapered sections of the balloon, and most preferably is greater than the wall thickness of the second layer along the proximal and distal tapered sections and/or the proximal and distal skirt sections of the balloon. The thickened wall portion of the balloon, resulting from the increased wall thickness of the second layer along the working length section, increases the strength of the balloon to thereby allow for expansion of the balloon to relatively large working diameters (e.g., greater than 3.0 mm), without resulting in disadvantageously thick sections of the balloon on either end of the working length section. Consequently, the stiffness of the distal end of the catheter at the balloon location is minimized. In a presently preferred embodiment, the wall thickness of the second layer of the balloon is greater than the wall thickness of the second layer along the proximal and/or distal tapered sections from the proximal to the distal end of the tapered section of the balloon (i.e., along the entire length of the proximal and distal tapered sections of the balloon).

In a presently preferred embodiment, the polymeric material forming the first layer of the balloon is a porous polymeric material such as expanded polytetrafluoroethylene (ePTFE), including ePTFE available from Zeus, Atrium Medical, Inertech, and IPE, and typically having an initial porosity of at least about 60%. However, a variety of suitable porous materials may be used including an ultra high molecular weight polyolefin such as ultra high molecular weight polyethylene, porous polyethylene, porous polypropylene, and porous polyurethane. In one embodiment, the porous material has a node and fibril microstructure. The node and fibril microstructure, when present, is produced in the material using conventional methods. ePTFE and ultra high molecular weight polyethylene (also referred to as "expanded ultra high molecular weight polyethylene") typically have a node and fibril microstructure, and are not melt extrudable. However, a variety of suitable polymeric materials can be used in the method of the invention including conventional catheter balloon materials which are melt extrudable. Typically, ePTFE is formed into a tubular balloon layer by bonding wrapped layers of the polymeric material together to form a tubular member, and not by conventional balloon blow molding. Although discussed primarily in terms of the embodiment in which the first layer of the balloon comprises ePTFE, it should be understood that a variety of suitable polymers may be used for the first layer. The second layer of the balloon prevents or inhibits inflation fluid from leaking out of the balloon interior through the porous polymeric material of the first layer, and is typically an inner layer or liner relative to the first layer of the balloon.

In a method of making a balloon of the invention, the second layer is formed of first and second sublayers of polymeric material placed one on top of the other, and typically fused together, to form the second layer having a thickened wall portion. However, a variety of methods can alternatively be used to make the balloon of the invention having a thickened wall portion. Forming the second layer by combining polymeric sublayers together to form the thickened polymeric wall portion is generally preferred over a method in which the ends of the second layer are thinned, as for example by necking or mechanically removing material therefrom, due to the ability to increase the wall thickness more precisely and without a decrease in the strength of the layer compared to the other methods.

The balloon catheter of the invention has excellent flexibility and improved balloon strength, with a low profile in the noninflated configuration, due to the configuration of the thickened wall portion of the balloon. Consequently, the catheter has excellent trackability (ability to track along the guidewire), and crossability (ability to cross a tight region of the blood vessel). These and other advantages of the invention will become more apparent from the following detailed description and accompanying exemplary drawings.

DETAILED DESCRIPTION OF THE PREFERRED EMBODIMENTS

Figure 1:
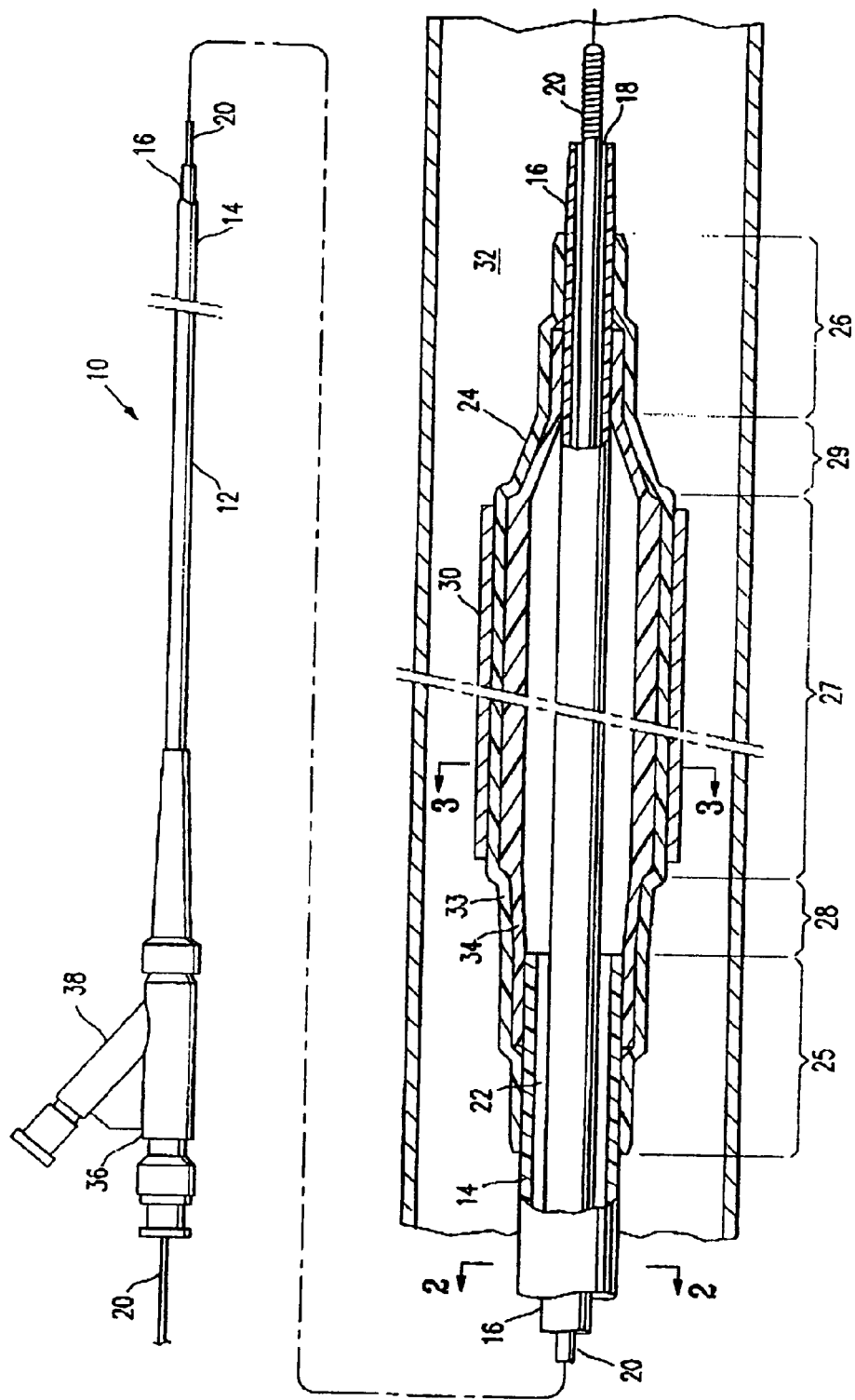
FIG. 1 is an elevational view, partially in section, of a stent delivery balloon catheter embodying features of the invention.
Figure 2:
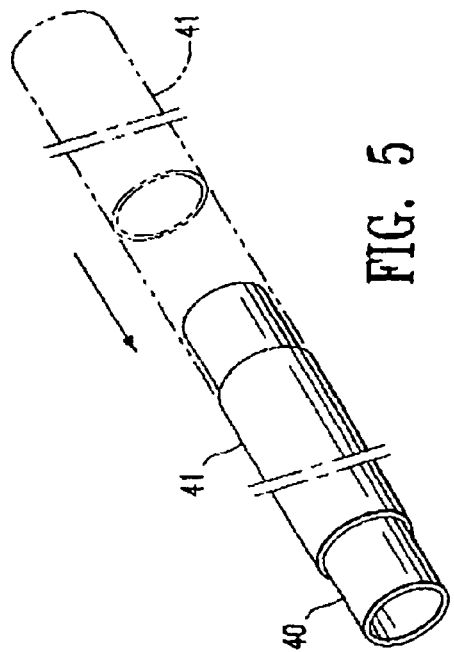
FIG. 2 is a transverse cross sectional view of the balloon catheter shown in FIG. 1, taken along line 2—2.
Figure 3:
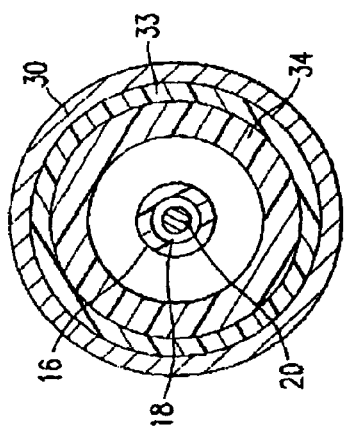
FIG. 3 is a transverse cross sectional view of the balloon catheter shown in FIG. 1, taken along line 3—3.

FIG. 1 illustrates an over-the-wire type stent delivery balloon catheter 10 embodying features of the invention. Catheter 10 generally comprises an elongated catheter shaft 12 having an outer tubular member 14 and an inner tubular member 16. Inner tubular member 16 defines a guidewire lumen 18 configured to slidingly receive a guidewire 20, and the coaxial relationship between outer tubular member 14 and inner tubular member 16 defines annular inflation lumen 22, as best shown in FIG. 2 illustrating a transverse cross section of the distal end of the catheter shown in FIG. 1, taken along line 2—2. An inflatable balloon 24 disposed on a distal section of catheter shaft 12 has a proximal skirt section 25 sealingly secured to the distal end of outer tubular member 14 and a distal skirt section 26 sealingly secured to the distal end of inner tubular member 16, so that the balloon interior is in fluid communication with inflation lumen 22. An adapter 36 at the proximal end of catheter shaft 12 is configured to provide access to guidewire lumen 18, and to direct inflation fluid through arm 38 into inflation lumen 22. In the embodiment illustrated in FIG. 1, the balloon 24 is illustrated prior to complete inflation thereof, with an expandable stent 30 mounted on the working length section of the balloon 24 for implanting within a patient's body lumen 32. The distal end of catheter 10 may be advanced to a desired region of the patient's body lumen 32 in a conventional manner, the balloon 24 inflated to expand stent 30, and the balloon deflated, leaving the stent 30 implanted in the body lumen 32.

In the embodiment of FIG. 1, balloon 24 has an outer layer 33 and an inner layer 34, extending from the proximal skirt section 25 to the distal skirt section 26. The inner surface of the outer layer 33 is preferably bonded to the inner layer 34, as for example by fusion bonding and/or adhesive bonding, and the balloon 24 is bonded to the shaft 12, preferably by fusion and/or adhesive bonding. For example, conventional adhesives such as light-cured (e.g., Dymax 204) and cyanoacrylates (e.g., Loctite 4011) may be used to bond layers 33, 34 to the shaft 12 at the proximal skirt section 25 and distal skirt section 26 of the balloon 24. In the embodiment illustrated in FIG. 1, the outer layer 33 of the balloon 24 has a proximal end section proximal to the inner layer 34 and bonded to the outer tubular member 14, and a distal end section distal to the inner layer 34 and bonded to the inner tubular member 16. The end sections of the outer layer 33, together with end sections of the inner layer 34 bonded to the shaft 12, form the proximal and distal skirt sections 25, 26, respectively. The proximal and distal skirt sections 25, 26 preferably have a length about equal to the minimum length required to provide a suitably strong bond between the balloon 24 and the shaft 12. The proximal end section and the distal end section of the inner layer 34 bonded to the shaft have a length of typically about 1 to about 5 mm, and the proximal end section and the distal end section of the outer layer 33 extending beyond the inner layer 34 and bonded to the shaft have a length of typically about 1 mm to about 4 mm, preferably about 1 mm to about 2 mm, for a balloon 24 having a length of about 8 to about 60 mm and a nominal outer diameter of about 2 to about 18 mm.

Balloon outer layer 33 comprises a porous polymeric material, and in one preferred embodiment a microporous polymeric material having a node and fibril microstructure such as ePTFE. Although discussed below primarily in terms of the embodiment in which the outer layer 33 is ePTFE, it should be understood that a variety of suitable materials can be used to form outer layer 33. The inner layer 34 is formed of a polymeric material preferably different from the polymeric material of the outer layer 33. Inner layer 34 limits or prevents leakage of inflation fluid through the microporous ePTFE to allow for inflation of the balloon 24. The inner layer 34 is preferably formed of an elastomeric material to facilitate deflation of the balloon 24 to a low profile deflated configuration, including polyurethanes, silicone rubbers, polyamide block copolymers, dienes, and the like. Inner layer 34 may consist of a separate layer which neither fills the pores nor disturbs the node and fibril structure of the ePTFE layer 33, or it may at least partially fill the pores of the ePTFE layer 33. The ePTFE layer 33 is preferably formed according to conventional methods, in which a sheet of ePTFE polymeric material is wrapped with overlapping or abutting edges to form a tubular body and then heated to fuse the wrapped material together. The ePTFE sheet is typically wrapped to form one or more layers, and preferably about two to about five layers, of wrapped material which are heated to fuse the layers together. The sheet of polymeric material preferably has the desired microstructure (e.g., porous and/or node and fibril) before being wrapped and heated on the mandrel. The resulting tube of ePTFE polymeric material is typically further processed by being stretched, sintered, compacted, and sintered again, to provide the desired properties such as the desired dimension, and dimensional stability (i.e., to minimize changes in length occurring during inflation of the balloon). The completed ePTFE layer 33 is then bonded to or otherwise combined with the elastomeric liner 34 either before or after layer 34 is bonded to the shaft.

Figure 4:
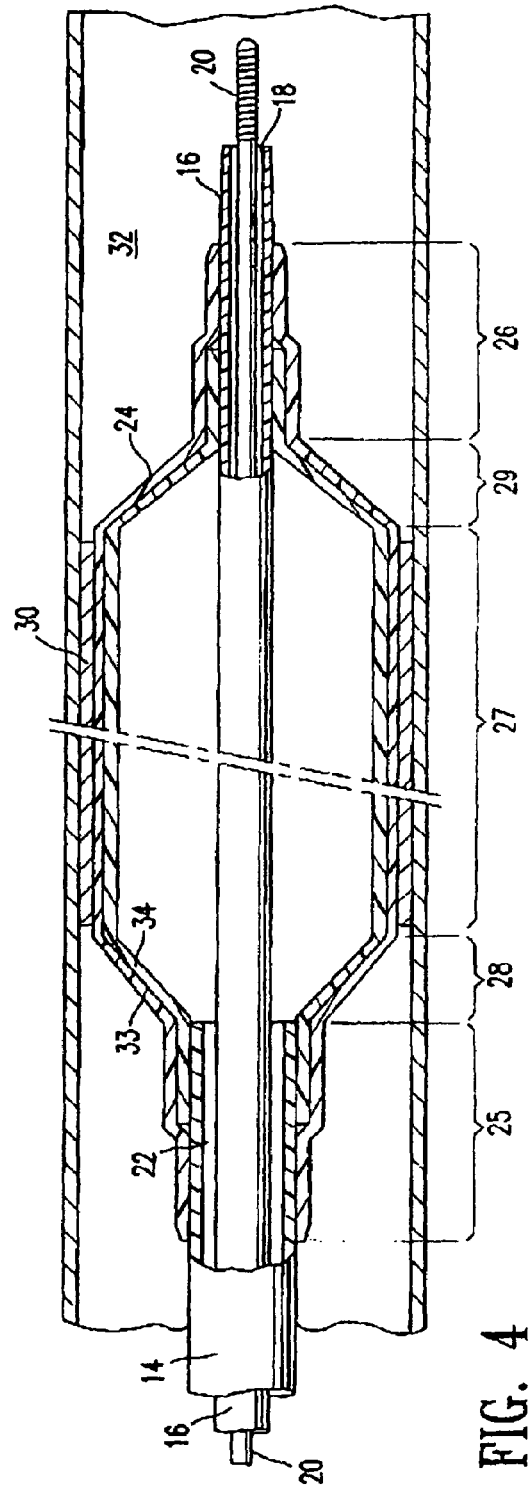
FIG. 4 illustrates the balloon catheter of FIG. 1, with the balloon in an inflated configuration to expand the stent within the patient's body lumen.

As best shown in FIG. 4 illustrating the distal end of the balloon catheter of FIG. 1 with the balloon 24 fully inflated in the body lumen 32 to expand the stent 30, the balloon 24 has a working length section 27, a proximal tapered section 28 between the proximal skirt section 25 and the working length 27, and a distal tapered section 29 between the distal skirt section 26 and the working length 27. The terminology "tapered section" should be understood to refer to the sections which are on either end of the central working length section and which inflate to a tapered shape (tapering from the inflated working length section down to the skirt section bonded to the shaft). In the embodiment of FIG. 4, the working length section 27 of the balloon 24 has a cylindrical, uniform outer diameter from the proximal to the distal end of the working length section in the inflated configuration, configured for receiving the tubular stent 30 thereon and expanding the stent 30 in the body lumen 32. However, a variety of suitable alternative working length section configurations can be used as are conventionally known.

As best illustrated in FIG. 1, inner layer 34 of balloon 24 has a thickened wall portion extending along the working length section 27 of the balloon 24. The wall thickness of the inner layer 34 along the working length section 27 of the balloon 24 is greater than the wall thickness of the remaining sections of the second layer 34 in the noninflated configuration. Specifically, the wall thickness of the second layer 34 along the entire length of the tapered sections 28, 29 from the proximal to the distal end thereof is less than the wall thickness of the second layer 34 along the entire length of the working length section 27 of the balloon in the noninflated configuration. Similarly, the wall thickness of the second layer 34 along the entire length of skirt sections 25, 26 is less than the wall thickness of the second layer 34 along the entire working length section 27 of the balloon 24 in the noninflated configuration.

In one embodiment, the wall thickness of the second layer 34 along the working length 27 is about 80% to about 120%, more specifically about 100% greater than the wall thickness of the second layer 34 along the proximal and distal skirt sections 28, 29 in the noninflated configuration. The thickened wall portion extending along the working length section 27 stretches as the balloon inflates to the inflated configuration and is consequently thinner than in the noninflated configuration. As a result, in one embodiment, the wall thickness of the second layer along the working length section 27 is the same or less than the wall thickness of the second layer along all or part of the tapered sections 28, 29 and/or the skirt sections 25, 26 of the balloon 24 in the inflated configuration.

In the illustrated embodiment, the second layer 34 in the noninflated configuration has a substantially uniform wall thickness (i.e., uniform within normal manufacturing tolerances) along the tapered sections 28, 29 of the balloon (i.e., from the skirt sections to the working length section 27), and along the skirt sections 25, 26 of the balloon. Consequently, in the noninflated configuration, the inflatable sections of the first layer 33 have a substantially uniform wall thickness, whereas the inflatable sections of the second layer 34 have a nonuniform wall thickness due to the larger wall thickness along the working length section 27.

Figure 5:
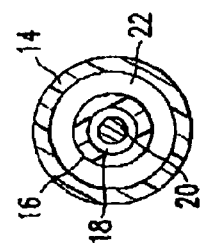
FIG. 5 illustrates formation of the balloon of FIG. 1 in a method embodying features of the invention.

FIG. 5 illustrates the formation of the balloon second layer 34, during one presently preferred method of making the balloon 24 of FIG. 1. The second layer 34 is formed by joining a first sublayer 40 to a second sublayer 41. The sublayers 40, 41 preferably comprise the same polymeric material (i.e., selected from the elastomeric polymers forming second layer 34 of the balloon 24, discussed above), so that the second layer is formed of a single polymeric material along the entire length and width of the second layer. Consequently, the sublayers 40, 41 readily fuse together when heated. The sublayers 40, 41 may alternatively be formed of different polymers, although the different polymers are preferably compatible (i.e., melt fusible) and, in one embodiment, have similar properties such as compliance and strength to prevent or inhibit producing a significant change in certain properties of the balloon, such as compliance, at the thickened wall portion. In the embodiment in which the sublayers 40, 41 are formed of the same polymer or highly compatible polymers, the sublayers soften and fuse together during heating, so that the resulting second layer 34 of the balloon 24 has a thickened wall portion due to the second sublayer 41 without a separation or seam present between the first and second sublayers 40, 41. Thus, a second layer 34 is formed which will extend between (and along) the proximal and distal skirt sections of the balloon and have a seamless increase in the wall thickness of the second layer along the central working length section.

The elastomeric polymeric material is typically hot melt extruded in the shape of a tube, to form the first and second sublayers 40, 41. The sublayers 40, 41 typically have the same wall thickness before being joined together, although the second sublayer 41 can alternatively be thicker or thinner than the first sublayer 40. In one embodiment, each sublayer 40, 41 has a thickness of about 0.004 to about 0.006 millimeter (mm), more specifically about 0.005 mm. The first sublayer 40 has a length about equal to the length of the second layer 34 of the balloon 24, and the second sublayer 41 has a length equal to the desired length of the working section 27 of the balloon 24 and is thus shorter than the first sublayer 40. Although illustrated with the second sublayer 41 on an outer surface of the first sublayer 40, the second sublayer 41 can alternatively be on an inner surface of the first sublayer 40. However, the embodiment having the second sublayer 41 on the outer surface of the first sublayer 40 is generally preferred to maximize the balloon inner diameter.

During formation of the balloon 24, the second sublayer 41 is slid over the first sublayer 40, to position it along the center of the length of the first sublayer 40, and the sublayers 40, 41 are heated to fuse the sublayers together to form the second layer 34 of the balloon 24. For example, with the proximal end of the first sublayer 40 bonded to the distal end of the outer tubular member 14, the second sublayer 41 is slid onto and in contact with the outer surface of the first sublayer 40. FIG. 5 illustrates the second sublayer 41 in position on the central section of the first sublayer 40, with the second sublayer 41 shown in phantom prior to being slid over the first sublayer 40. The first layer 33 of the balloon is then slid over the first and second sublayers 40, 41 forming a balloon subassembly, and the proximal end of the first layer 33 is bonded to the distal end of the outer tubular member 14 to complete the formation of the balloon proximal skirt section 25. With the inner tubular member 16 in position extending through the balloon subassembly interior, the distal ends of the first layer 33 and the first sublayer 40 of the second layer 34 are bonded to the inner tubular member 16 to form the distal skirt section 26 of the balloon 24. The balloon subassembly is then heated to bond the sublayers 40, 41 together and to join the resulting layer 34 to outermost layer 33. For example, the layers are heated, typically with a radially inward force applied to the outer surface of the balloon subassembly such as by a collet-like mold, to heat and press the layers together. A very minor increase in pressure such as about 2 atm can be applied in the interior of the balloon subassembly attached to the shaft 12 during the heating of the layers 33, 34 together, to prevent or inhibit wrinkles in the layers of the balloon. An adhesive and/or surface treatment is typically used to enhance bondability of the outer layer 33 in the embodiment in which the outer layer is a low surface energy material such as ePTFE. The resulting balloon 24 has a thickened wall portion due to the presence of the second sublayer 41, forming a stepwise increase in the wall thickness and outer diameter of the balloon 24 at the ends of the working length section 27.

The dimensions of catheter 10 are determined largely by the size of the balloon and guidewire to be employed, the catheter type, and the size of the artery or other body lumen through which the catheter must pass or the size of the stent being delivered. Typically, the outer tubular member 14 has an outer diameter of about 0.025 to about 0.04 inch (0.064 to 0.10 cm), usually about 0.037 inch (0.094 cm), and the wall thickness of the outer tubular member 14 can vary from about 0.002 to about 0.008 inch (0.0051 to 0.02 cm), typically about 0.003 to 0.005 inch (0.0076 to 0.013 cm). The inner tubular member 16 typically has an inner diameter of about 0.01 to about 0.018 inch (0.025 to 0.046 cm), usually about 0.016 inch (0.04 cm), and a wall thickness of about 0.004 to about 0.008 inch (0.01 to 0.02 cm). The overall length of the catheter 10 may range from about 100 to about 150 cm, and is typically about 143 cm. Preferably, balloon 24 has a length about 0.8 cm to about 6 cm, and an inflated working diameter of about 2 to about 8 mm.

Inner tubular member 16 and outer tubular member 14 can be formed by conventional techniques, for example by extruding and necking materials already found useful in intravascular catheters such a polyethylene, polyvinyl chloride, polyesters, polyamides, polyimides, polyurethanes, and composite materials. The various components may be joined using conventional bonding methods such as by fusion bonding or use of adhesives. In the embodiment illustrated in FIG. 1, the outer and inner tubular members 14, 16 are each formed of a single-layered, uniform polymeric member. However, it should be understood that in alternative embodiments, one or both of the outer and inner tubular members 14, 16 may be a multilayered, multisectioned, and/or blended polymeric member. Although the shaft is illustrated as having an inner and outer tubular member, a variety of suitable shaft configurations may be used including a dual lumen extruded shaft having a side-by-side lumens extruded therein. Similarly, although the embodiment illustrated in FIG. 1 is an over-the-wire stent delivery catheter, balloons of this invention may also be used with other types of intravascular catheters, such as rapid exchange type balloon catheters.

While the present invention is described herein in terms of certain preferred embodiments, those skilled in the art will recognize that various modifications and improvements may be made to the invention without departing from the scope thereof. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

What is claimed:

1. A balloon catheter, comprising
 a) an elongated shaft having a proximal end, a distal end, and at least one lumen; and
 b) a balloon having a proximal and a distal skirt section secured to the shaft so that an interior of the balloon is in fluid communication with the at least one lumen of the shaft, and having a noninflated configuration, an inflated configuration, a working length section, a proximal tapered section having a proximal end at a distal end of the proximal skirt section and a distal end at a proximal end of the working length section, a distal tapered section having a proximal end at a distal end of the working length section and a distal end at a proximal end of the distal skirt section, a first layer formed of a first polymeric material, and a second layer formed of a second polymeric material different from the first polymeric material, the first and second layers extending from the proximal skirt section to the distal skirt section of the balloon, such that the second polymeric material extends from the proximal to the distal skirt section of the balloon, the second layer having a wall thickness, the wall thickness of the second layer along the entire working length section from the proximal to the distal end of the working length section being greater than the wall thickness of the second layer along at least one of the proximal tapered section and the distal tapered section of the balloon from the proximal to the distal end of the tapered section in the noninflated configuration, so that the working length section defines a thickened wall portion of the balloon.

2. The balloon catheter of claim 1 wherein the wall thickness of the second layer along the working length section is greater than the wall thickness of the second layer along both the proximal and the distal tapered sections from the proximal to the distal end of the tapered sections in the noninflated configuration.

3. The balloon catheter of claim 2 wherein the working length section has a cylindrical, uniform outer diameter from the proximal to the distal end of the working length section in the inflated configuration.

4. The balloon catheter of claim 1 wherein the wall thickness of the second layer along the working length is greater than the wall thickness of the second layer along the proximal and distal skirt sections of the balloon in the noninflated configuration.

5. The balloon catheter of claim 4 wherein the wall thickness of the second layer along the working length is about 80% to about 120% greater than the wall thickness of the second layer along the proximal skirt section in the noninflated configuration.

6. The balloon catheter of claim 1 wherein the second layer wall thickness is substantially uniform along the proximal tapered section in the noninflated configuration.

7. The balloon catheter of claim 1 wherein the second layer wall thickness is substantially uniform along the distal tapered section in the noninflated configuration.

8. The balloon catheter of claim 1 wherein the second layer comprises a first sublayer formed of the second polymeric material, and a second sublayer formed of the second polymeric material fused to an outer surface of the first sublayer along a central section of the first sublayer.

9. The balloon catheter of claim 1 wherein the second layer is an inner layer relative to the first layer.

10. The balloon catheter of claim 1 wherein the first layer is a porous polymeric material selected from the group consisting of expanded polytetrafluoroethylene, ultra high molecular weight polyolefin, ultra high molecular weight polyethylene, porous polyethylene, porous polypropylene, and porous polyurethane.

11. The balloon catheter of claim 1 wherein the second layer is formed of a single polymeric material along the entire length and width of the second layer.

12. The balloon catheter of claim 1 wherein the balloon catheter is a stent delivery catheter system, and including a stent mounted on the working length section of the balloon in the noninflated configuration with a proximal and a distal end of the stent located on the thickened wall portion of the balloon.

13. A balloon catheter, comprising:
a) an elongated shaft having a proximal end, a distal end, and at least one lumen; and
b) a balloon having a proximal and a distal skirt section secured to the shaft so that an interior of the balloon is in fluid communication with the at least one lumen of the shaft, and having a noninflated configuration, an inflated configuration, a working length section, a proximal tapered section having a proximal end at a distal end of the proximal skirt section and a distal end at a proximal end of the working length section, a distal tapered section having a proximal end at a distal end of the working length section and a distal end at a proximal end of the distal skirt section, a first layer formed of a porous polymeric material, and a second layer formed of an elastomeric polymeric material different from the porous polymeric material, the first and second layers extending from the proximal to the distal skirt sections of the balloon, the second layer having a wall thickness, the wall thickness of the second layer along the entire working length section from the proximal to the distal end thereof being greater than the wall thickness of the second layer along the proximal and distal skirt sections in the noninflated configuration, so that the working length section defines a thickened wall portion of the balloon.

14. The balloon catheter of claim 13 wherein the wall thickness of the second layer along the working length section is greater than the wall thickness of the second layer along the proximal tapered section and the distal tapered section of the balloon from the proximal to the distal end of the tapered sections in the noninflated configuration.

* * * * *